United States Patent [19]

Dell et al.

[11] Patent Number: 4,614,741
[45] Date of Patent: Sep. 30, 1986

[54] DEPOT ANTIINFLAMMATORY AGENTS

[75] Inventors: Hans-Dieter Dell, Berg.-Gladbach; Bernhard Pelster, St. Augustin; Reinhold Kraus, Cologne; Detlef Schierstedt, St. Augustin, all of Fed. Rep. of Germany

[73] Assignee: Troponwerke GmbH & Co., KG, Cologne, Fed. Rep. of Germany

[21] Appl. No.: 622,423

[22] Filed: Jun. 20, 1984

[30] Foreign Application Priority Data

Jul. 5, 1983 [DE] Fed. Rep. of Germany ....... 3324193

[51] Int. Cl.$^4$ .................... A61K 31/40; A61K 31/54; A61K 31/195
[52] U.S. Cl. .................................. 514/222; 514/420; 514/561

[58] Field of Search ................ 424/274; 514/420, 222, 514/561

[56] References Cited

U.S. PATENT DOCUMENTS 4,269,828  5/1981  Flora et al. ......................... 424/274

Primary Examiner—Stanley J. Friedman
Attorney, Agent, or Firm—Sprung Horn Kramer & Woods

[57] ABSTRACT

The invention relates to depot formulations containing, as an active antiinflammatory and/or analgesic agent a compound of Formula I, infra together with a suspension medium. Typical suspension agents are glycerides and/or esters of mono- or poly-hydric alcohols as well as selected ethers, alcohols and amides.

4 Claims, No Drawings

DEPOT ANTIINFLAMMATORY AGENTS

The present invention relates to depot formulations containing a compound of the formula I

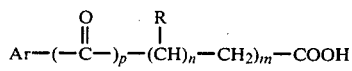

$$Ar-(-\overset{O}{\underset{\|}{C}}-)_p-(\overset{R}{\underset{|}{CH}})_n-CH_2)_m-COOH \quad \text{I}$$

in which

R represents hydrogen, lower alkyl or substituted alkyl,

Ar represents aryl, heteroaryl, substituted aryl or substituted heteroaryl, and m and/or n can be zero, or n+m are the numbers 1–2, and p is zero or 1, and their alkyl-, aryl-, aralkyl- or heteroaryl-esters, amides mono- or dialkylamides, mono- or diarylamides, mono- or diaralkylamides or mono- or diheteroarylamides in which the alkyl chains have 1 to 6C-atoms, amides or salts.

Antiinflammatory-analgesic active compounds have hitherto been used in warm-blooded animals with oral, rectal, cutaneous and intramuscular administration. The administration regimen of these depends crucially on the biological half-life and the duration of action. Multiple administration each day is necessary with many of these medicaments.

To prolong the duration of action, many active compounds have been described as retard products in specific pharmaceutical formulations, for example 1-(p-chlorobenzoyl)-5-methoxy-2-methylindole-3-acetic acid as a sustained release product in U.S. Pat. No. 4,173,626.

There has not hitherto been an antiinflammatory analgesic in depot form which still displays a sufficient effect on administration at intervals of several days.

Thus the object of the present invention was to make available an antiinflammatory/analgesic in depot form.

The invention is based on the fact that it has been found, surprisingly, that compounds of the general formula I have, when used intramuscularly in a suitable form, a potent antiinflammatory effect over a considerably longer period than the same active compounds in, for example, a form for oral administration.

Thus, the present invention relates to agents containing at least one compound of the formula I and a suspending medium, and to a process for the preparation of these agents, and to the use of these agents as a depot antiinflammatory or depot analgesic.

The depot formulations contain at least one of the compounds of the formula I together with a suspending medium. The following are to be understood as suspending media in the sense of the present invention: triglycerides with monocarboxylic and dicarboxylic acids of chain lengths $C_6$ to $C_{20}$ in saturated or unsaturated, optionally also hydroxylated, form (especially oily triglycerides, such as viscoleo, and cottonseed, groundnut, maize germs, almond, olive, castor and sesame oil). Also suitable are esters of monohydric or polyhydric alcohols, for example propylene glycol, butanediols and higher alkanols, alkanediols, of chain length $C_2$–$C_{30}$ with the abovementioned acid components (the following may be mentioned as examples: ethyl oleate, isopropyl myristate and isopropyl stearate) and furthermore benzylbenzoate and glycofurate.

In place of or in addition to suitable esters, the suspending medium can also contain ethers, alcohols and amides (saturated and unsaturated, aliphatic or aromatic), and the amides can also be cyclised, for example 2-pyrrolidone (as a monomer or polymer) which are toxicologically innocuous. The proportion of the suspending medium in the depot formulation according to the invention is between 2 and 90%, preferably 3–70%, particularly preferably 10–60% by weight.

The sterile solutions or suspensions for injection purposes can also contain gelling agents, for example aluminium stearate, to retard the release from the oil depot.

Where appropriate, one or more preservatives can be used, for example benzyl alcohol, phenylethyl alcohol, chlorobutanol and chlorocresol. Where appropriate, one or more antioxidants are added to the suspending medium, for example, tocopherols, noridhydroguaiaretic acid, 2- and 3-tert.butyl-4-hydroxy-amide, ascorbic acid, propyl, octyl, dodecyl-gallate and butylhydroxytoluene.

Where appropriate, it is also possible for the depot products to exist initially in a separated form (active compound/dissolving or suspending medium) and to be mixed before use (for example dry ampoules).

According to the invention, the following are to be understood as compounds of the general formula I:

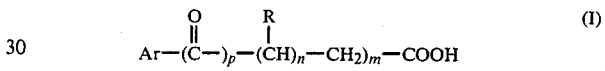

$$Ar-(-\overset{O}{\underset{\|}{C}}-)_p-(\overset{R}{\underset{|}{CH}})_n-CH_2)_m-COOH \quad (I)$$

in which

R represents hydrogen, lower alkyl or substituted alkyl,

Ar represents aryl, heteroaryl, substituted aryl or substituted heteroaryl, and m and/or n can be zero, n+m are the numbers 1–2, and p is zero or 1, and their alkyl-, aryl-, aralkyl- or heteroaryl-esters, amides, mono- or dialkylamides, mono- or diarylamide, mono- or diaralkylamides or mono- or diheteroarylamides in which the alkyl chains have 1 to 6C-atoms, amides or salts. R is alkyl is one having 1 to 6C-atoms, and substituted alkyl denotes alkoxyalkyl.

Aryl or heteroaryl, as used herein, preferably denote phenyl, naphthyl, thiophenyl, pyrrolyl, indenyl, indolyl, benzothiazinyl or phenothiazinyl.

Those compounds of the formula I in which

R represents H, alkyl having 1–4C atoms or substituted alkyl, n and/or m can be zero, or n+m are the numbers 1–2, and p is zero or 1 are to be understood as preferred.

Ar represents aryl, heteroaryl and their substituted derivatives, preferred suitable substituents for aryl or heteroaryl being alkyl, preferably straight-chain and branched alkyl having up to 6C atoms, alkoxy, hydroxyalkyl, acyl, hydroxyl, acetoxy, benzoyl, substituted benzoyl, phenyl, substituted phenyl, phenoxy, halogen and phenylalkenyl, Apart from the acids, their esters, amides and salts are also suitable.

The esters are alkyl esters having 1–6C atoms, preferably methyl, ethyl, i- and n-propyl, substituted alkyl, for example β-hydroxyethyl, esters with glycolic acid. The amides can also contain lower alkyls or substituted alkyls in place of one or both amide hydrogens in the group —CO—NH$_2$.

Examples of salts are those with alkali metals, alkaline earth metals, aluminium etc.

Among the depot formulations according to the invention, those which contain as active compound at least one of the following compounds:

| | | |
|---|---|---|
| 1. | 2-Hydroxybenzoic acid | 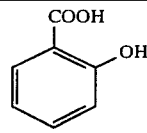 |
| 2. | Acetoxybenzoic acid | 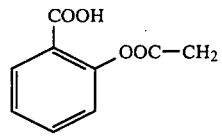 |
| 3. | 2',4'-Difluoro-4-hydroxy-3-biphenyl-carboxylic acid | 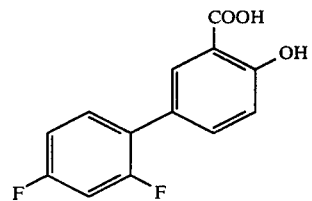 |
| 4. | 2-Hydroxybenzamide | 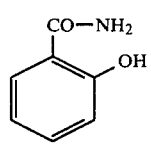 |
| 5. | [2-(Aminocarbonyl)-phenoxy]acetic acid | 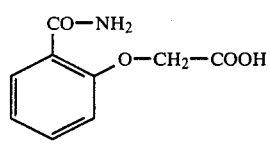 |
| 6. | 4-Allyloxy-3-chloro-phenylacetic acid | 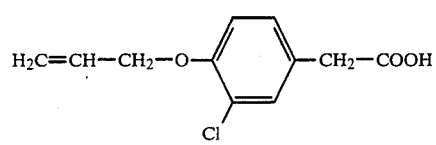 |
| 7. | 2-[(2,6-Dichloro-phenyl)amino]phenyl-acetic acid | 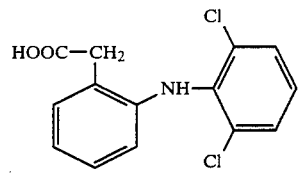 |
| 8. | 10-Methylphenothiazin-2-yl-acetic acid | 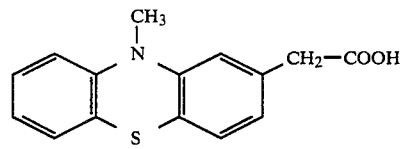 |
| 9. | 1-Methyl-5-(p-toluoyl)-2-pyrrolyl-acetic acid | 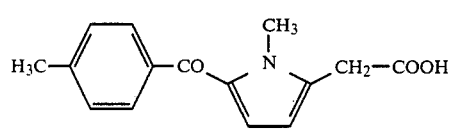 |
| 10. | D-2-(6-Methoxy-2-naphthyl)propionic acid | 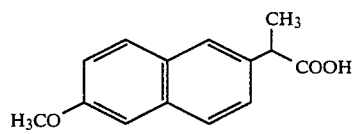 |

-continued
| | | |
|---|---|---|
| 11. | 2-(p-Isobutylphenyl)-propionic acid | 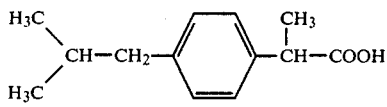 |
| 12. | 2-(3-Phenoxyphenyl)-propionic acid | 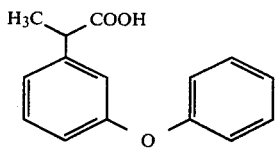 |
| 13. | 2-(m-Benzoylphenyl)-propionic acid | 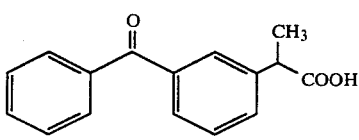 |
| 14. | 2-[4-(1-Oxo-2-isoindolinyl)-phenyl]propionic acid | 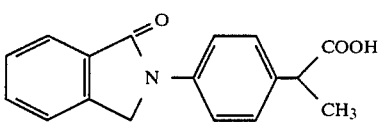 |
| 15. | 2-(2-Fluoro-4-biphenylyl)-propionic acid | 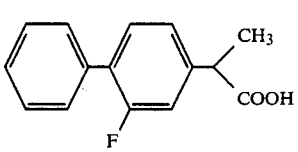 |
| 16. | 3-(4-Biphenylylcarbonyl)-propionic acid | 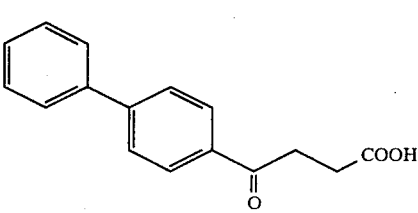 |
| 17. | 2-(5-Benzoyl-2-thienyl)-propionic acid | 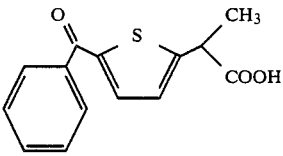 |
| 18. | 1-(p-Chlorobenzoyl)-5-methoxy-2-methylindole-3-acetic acid | 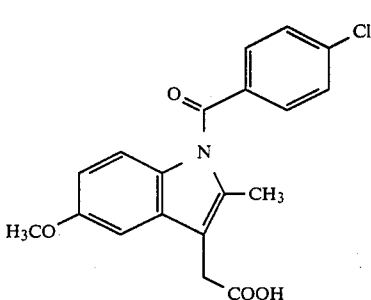 |

| | | |
|---|---|---|
| | -continued | |
| 19. | [1-(p-Chlorobenzoyl-5-methoxy-2-methylindole-3-acetoxy]acetic acid | 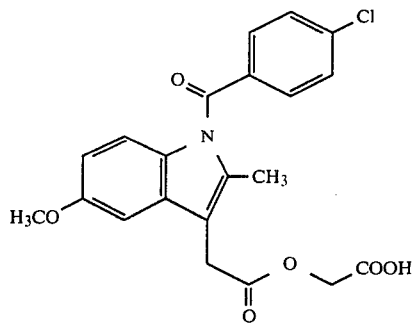 |
| 20. | (Z)-5-Fluoro-2-methyl-1-{[(4-methylsulphinyl)-phenyl]methylene}-1H—indene-3-acetic acid | 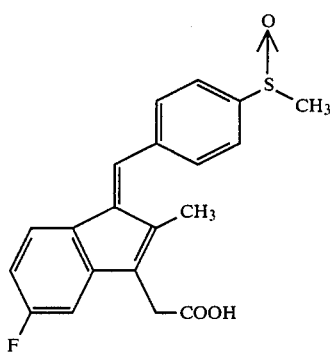 |
| 21. | 4-Hydroxy-2-methyl-N—2-thiazolyl-2H—1,2-benzothiazine-3-carboxymide 1,1-dioxide | 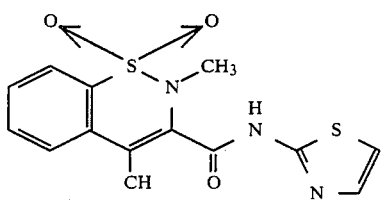 |
| 22. | 4-Hydroxy-2-methyl-N—2-pyridinyl-2H—1,2-benzothiazine-3-carboxamide 1,1-dioxide | 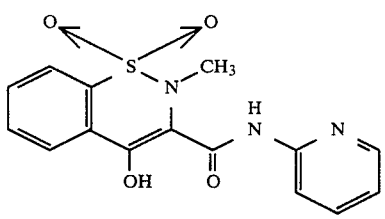 |
| 23. | 4-Butyl-1,2-diphenyl-3,5-pyrazolidindione | 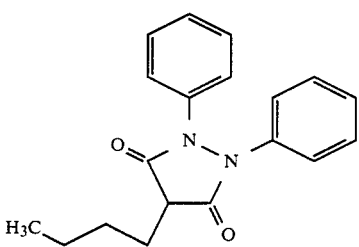 |

| | -continued | |
|---|---|---|
| 24. | 4-n-Butyl-1-(p-hydroxy-phenyl)-2-phenyl-pyrazolidindione | 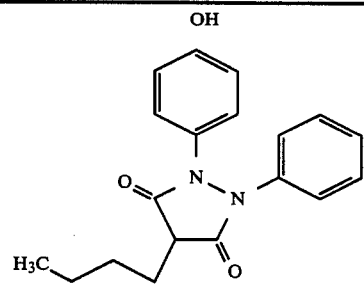 | are to be understood as very particularly preferred.

Where appropriate, it is also possible to use the alkyl esters, hydroxyalkyl esters and hydroxyalkoxyalkyl esters of these acids and substituted amides or salts.

The pharmacologically active compounds of the general formula I are contained in the depot agents according to the invention in amounts of from 3 to 80% by weight, preferably from 5 to 75% by weight, particularly preferably at 10 to 70% by weight.

The depot preparations contain, in a very particularly preferred manner, at least one of the following group as the suspending medium: viscoleo, isopropyl myristate, ethyl oleate, castor oil, sesame oil, arachis oil, cottonseed oil, almond oil, olive oil, neatsfoot oil, neutral oil and maize oil.

Viscoleo is to be understood to be a mixture of triglycerides of saturated fatty acids of medium chain length which is neutral and liquid at room temperature. In particular, viscoleo is to be understood to be a mixture of triglycerides of saturated fatty acids in a nutric acids are: caprylic (45–60%), caprinic acid (35–50%) and laurinic acid (2–10%).

Neatsfoot oil is to be understood as the pale yellow coloured oil which has only a faint odour and is obtained by extraction by boiling the hooves of cattle or sheep of horses with water, neutral oil, for example miglyol, is caprylic/capric acid triglyceride, a liquid of low viscosity.

Apart from the active compounds of the general formula I, the depot agents according to the invention can also contain other pharmaceutically active compounds.

The preparation of the formulations described above is carried out by vigorously mixing the active compound or compounds of the general formula I with the suspending medium in the ratios of amounts indicated above.

Solutions are normally prepared by dissolving the active compounds and auxiliaries which are sterile or have a low organism count in the sterilised solvent. The solution is then sterilised by filtration and filled into ampoules.

The suspension are prepared from sterile active compounds and auxiliaries under aseptic conditions. Where appropriate, these operations (with solution and suspension) are carried out under protective gas, and heat sterilisation is possible in particular cases.

The ampoules contain 0.5–5.0 ml. The solution or suspension to be administered is preferably 1–3 ml, particularly preferably 1–2 ml.

The antioedemic and analgesic effect of the test substances after i.m. administration of an appropriate depot formulation was determined using the carrageenan-induced oedema of the rat paw or using the Randall-Selitto test [Arch. int. Pharmacodyn. 111, 409 (1957)].

The tests were carried out with male rats [strain: Bor:WISW (SPF-Cpb), weight about 200 g]. The animals receive a single i.m. administration of a depot product, and the antiinflammatory effect was checked on subsequent days by inducing oedema with carrageenan. Three groups each containing 5 animals were investigated in each day, the first group comprising 5 untreated animals, the 2nd group comprising 5 animals treated only with solvent (for example viscoleo) and the 3rd group comprising 5 animals treated with depot product (for example 4-hydroxy-2-methyl-N-2-pyridinyl-2H-1,2-benzothiazine-3-carboxamide, 1,1-dioxide, formula 22, in viscoleo).

The paw volumes were measured by the method of F. Kemper and G. Ameln [Z. ges. exp. Med. 131, 407 (1959)], the difference between the volume of the paw 5 hours after provocation of oedema and the normal volume of the paw giving the volume of the oedema.

The inhibition of carrageenan-oedema after i.m. administration of various active compounds as solutions or suspensions in an oily medium was determined 2 and 4 days after the injection. Various doses were administered in a constant volume of 0.03 ml administered per rat (see Table).

| | % inhibition of oedema | |
|---|---|---|
| Substance (mg/kg) | 2nd | 4th day after inj. |
| 1-(p-Chlorobenzoyl)-5-methoxy-2-methylindole-3-acetic acid (18) (10.0 mg/kg), suspension | 58.2 | 29.5 |
| 2'-4'-Difluoro-4-hydroxy-3-biphenylcarboxylic acid (3) (5 mg/kg), suspension | 26 | 13 |
| 2-(p-Isobutylphenyl)-propionic acid (11) (13 mg/kg), suspension | 40 | 45 |
| D-2-(6-Methoxy-2-naphthyl)-propionic acid (10) (2.5 mg/kg), suspension | 42.8 | 22.3 |
| 4-Hydroxy-2-methyl-N—2-pyridinyl-2H—1,2-benzothiazine-3-carboxamide 1,1-dioxide (22) (0.6 mg/kg), suspension | 33 | 39 |
| 4-Hydroxy-2-methyl-N—2-thiazolyl-2H—1,2-benzothiazine-4-carboxamide 1,1-dioxide (21) (15 mg/kg), suspension | 42.9 | 30.4 |
| 1-(p-Chlorobenzoyl)-5-methoxy-2-methylindole-3-acetic acid (18) (10.0 mg/kg), solution | 58.2 | 29.5 |
| 4-Hydroxy-2-methyl-N—2-pyridinyl-2H—1,2-benzothiazine-3-carboxamide 1,1-dioxide (22) (0.6 mg/kg), solution | 33.2 | 39.3 |

In the same model (oedema of the rat paw), p.o. administration of these active compounds led to great inhibition of oedema (H. Jacobi et al., Arzneimittelforsch. 27 1328 (1977) and 30, 1326 (1980)). However, after p.o. administration, in contrast to the depot preparations according to the invention, this was in the region of the control figures on the 2nd day after administration.

In contrast to the prolongation of the effect after i.m. administration of the depot preparations according to the invention, comparison of the biological half-lives of antiinflammatories after p.o. administration and i.m. administration in aqueous solution shows that there is no difference in the half-life in the latter case.

Thus, T. Ishizaki et al., (Eur. J. Clin. Pharmacol., 18, 407–414 (1980) describe the biological half-life of compound 13 in humans as being 1.13±0.07 hours after p.o. administration, and 1.27÷0.04 hours after i.m. administration in aqueous solution; nor do the maximum level in the plasma, or the plasma and renal clearance differ.

The present invention also includes the use of the depot products in human and veterinary medicine for controlling inflammatory and/or painful processes.

In general, it is advisable in medicine to administer the active compounds according to the invention in total amounts of about 0.1 to about 100, preferably 0.3 to 10, mg/kg of body weight per injection. However, it can be necessary to deviate from the dosages mentioned, and in particular to do so as a function of the nature and body weight of the subject to be treated, and the nature and severity of the illness.

The examples which follow illustrate injectable oily solutions or suspensions, according to the invention, which can be employed as depot antiinflammatories or depot analgesics, and which represent particularly preferred compositions:

TABLE 1

| | Examples of suspensions | |
|---|---|---|
| 1 | 1-(p-Chlorobenzoyl)-5-methoxy-2-methylindole-3-acetic acid (formula 18) | 200 g |
| | Isopropyl myristate | ad 1,000 g |
| 2 | [1-(p-Chlorobenzoyl)-5-methoxy-2-methylindole-3-acetoxy]acetic acid, formula 19, | 200 g |
| | Isopropyl myristate | ad 1,000 g |
| 3 | 4-Hydroxy-2-methyl-N—2-pyridinyl-2H—1,2-benzothiazine-3-carboxamide 1,1-dioxide, formula 22, | 30 g |
| | Aluminium stearate | 20 g |
| | Viscoleo | ad 1,000 g |
| 4 | 4-Hydroxy-2-methyl-N—2-thiazolyl-2H—1,2-benzothiazine-3-carboxamide 1,1-dioxide, formula 21 | 30 g |
| | Aluminium stearate | 20 g |
| | Viscoleo | ad 1,000 g |
| 5 | (Z)-5-Fluoro-2-methyl-1{[(4-methylsulphinyl)phenyl]methylene}-1H—indene-3-acetic acid, formula 20 | 200 g |
| | Miglyol 812 | ad 1,000 g |
| 6 | 2-(m-Benzoylphenyl)propionic acid, formula 13 | 250 g |
| | Miglyol 812 | ad 1,000 g |
| 7 | 2-(2-Fluoro-4-biphenylyl)propionic acid, formula 15 | 250 g |
| | Propyl gallate | 10 g |
| | Sesame oil | ad 1,000 g |

TABLE 2

| | Examples of oily solutions | |
|---|---|---|
| 1 | 4-Hydroxy-2-methyl-N—-2-pyridinyl-2H—1,2-benzothiazine-3-carboxamide | 13.0 g |

TABLE 2-continued

| | Examples of oily solutions | |
|---|---|---|
| | 1,1-dioxide, formula 22 | |
| | Laktonal | 131.5 g |
| | 2-Pyrrolidone | 255.5 g |
| | Miglyol 840 | ad 1,000.0 g |
| 2 | 1-(p-Chlorobenzoyl)-5-methoxy-2-methylindole-3-acetic acid, formula 18 | 150.0 g |
| | Laktonal | 112.0 g |
| | 2-Pyrrolidone | 300.0 g |
| | Miglyol 840 | ad 1,000.0 g |
| 3 | 2-(m-Benzoylphenyl)propionic acid, formula 13, | 100.0 g |
| | Laktonal | 90.0 g |
| | 2-Pyrrolidone | 250.0 g |
| | Myglyol 840 | ad 1,000.0 g |

Miglyol 840 is understood to be the propylene glycol derivatives of caprylic and capronic acids.

The solutions are normally prepared by dissolving the active compounds and auxiliaries, which are sterile or have a low organism count, in the sterilised solvent. The solution is then sterilised by filtration and filled into ampoules.

The suspensions are prepared from sterile active compounds and auxiliaries under aseptic conditions. Where appropriate, the operations are carried out (with solution and suspension) under a protective gas, and heat sterilisation is possible in special cases.

| Arachis oil | = Ol. arachidis neutralisatum |
|---|---|
| Cottonseed oil | = Ol. gossypii neutralisatum |
| Almond oil | = Ol. amygdalae neutralisatum |
| Olive oil | = Ol. olivae neutralisatum |
| Sesame oil | = Ol. sesami neutralisatum |
| Castor oil | = Ol. ricini neutralisatum |
| Neatsfoot oil | = Ol. pedis bovis/equi |
| Neutral oil | = Ol neutrale (for example miglyol) |
| Maize oil | = Ol. maydis neutralisatum |

The intention is to illustrate the present invention in more detail by the examples which follow.

TABLE 3

(Oily solutions of D-2-(6-methoxy-2-naphthyl-propionic acid

| Example | [mg] | Dissolving or suspending medium [ad 1000 mg] | Propyl gallate [mg] | Al stearate [mg] | Neutral oil [mg] |
|---|---|---|---|---|---|
| 11 | 270 | Arachis oil | 10 | | |
| 12 | 100 | Arachis oil | 10 | | |
| 13 | 260 | Cottonseed oil | | | |
| 14 | 100 | Cottonseed oil | | 20 | |
| 15 | 260 | Almond oil | | | |
| 16 | 100 | Almond oil | | | |
| 17 | 270 | Maize oil | | | |
| 18 | 100 | Maize oil | | | |
| 19 | 280 | Olive oil | 10 | | |
| 20 | 100 | Olive oil | 10 | | |
| 21 | 250 | Castor oil | 10 | | |
| 22 | 100 | Castor oil | 10 | | |
| 23 | 260 | Sesame oil | | | |
| 24 | 100 | Sesame oil | | | |
| 25 | 270 | Neatsfoot oil | | | |
| 26 | 100 | Neatsfoot oil | | 20 | |
| 27 | 180 | Neutral oil | | | |
| 28 | 100 | Neutral oil | | 20 | |
| 29 | 280 | Ethyl oleate | | | |
| 30 | 100 | Ethyl oleate | | | |
| 31 | 280 | Isopropy myristate | | | |
| 32 | 100 | Isopropy myristate | | 20 | |
| 33 | 280 | Isopropyl palmitate | | | |
| 34 | 100 | Isopropyl pamitate | | | |
| 35 | 250 | Oleyl oleate | | | |

TABLE 3-continued (Oily solutions of D-2-(6-methoxy-2-naphthyl-propionic acid

| Example | [mg] | Dissolving or suspending medium [ad 1000 mg] | Propyl gallate [mg] | Al stearate [mg] | Neutral oil [mg] |
| --- | --- | --- | --- | --- | --- |
| 36 | 100 | Oleyl oleate | | | |
| 37 | 250 | Benzyl benzoate | | | 250 |
| 38 | 90 | Benzyl benzoate | | | 500 |
| 39 | 250 | Poppyseed oil | 10 | | |
| 40 | 90 | Poppyseed oil | 10 | | |
| 41 | 260 | Viscoleo | | | |
| 42 | 100 | Viscoleo | | 20 | |

In analogy to Table 3, the following compounds have also been employed as the active compound in each case:

13: 2-(m-Benzoylphenyl)propionic acid
15: 2-(2-Fluoro-4-biphenylyl)propionic acid
17: 2-(5-Benzoyl-2-thienyl)propionic acid
18: 1-(p-Chlorobenzoyl)-5-methoxy-2-methylindole-3-acetic acid
19: [1-(p-Chlorobenzoyl)-5-methoxy-2-methylindole-3-acetoxy]acetic acid
20: (Z)-5-Fluoro-2-methyl-1-{[(4-methylsulphinyl)-phenyl]methylene}-1H-indene-3-acetic acid
21: 4-Hydroxy-2-methyl-N-2-pyridinyl-2H-1,2-benzothiazine-3-carboxamide 1,1-dioxide
22: 4-Hydroxy-2-methyl-N-2-thiazolyl-2H-1,2-benzothiazine-3-carboxamide 1,1-dioxide
23: 4-Butyl-1,2-diphenyl-3,5-pyrazolidindione
24: 4-n-Butyl-1-(p-hydroxyphenyl)-2-phenyl-pyrazolidindione.

What is claimed is:

1. An injectable antiinflammatory agent containing 10–70% by weight of active compound of the formula

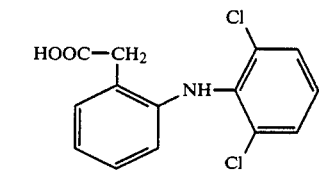

and 10–60% by weight of suspending agent selected from the group consisting of biscoleo, isopropyl myristate, ethyl oleate, castor oil, sesame oil, arachis oil, cottonseed oil, almond oil, olive oil, neatsfoot oil, neutral oil and maize oil.

2. An injectable antiinflammatory agent containing 10–70% by weight of active compound of the formula 3. An injectable antiinflammatory agent of claim 1 wherein the suspending agent is isopropyl myristrate.

4. An injectable antiinflammatory agent of claim 2 wherein the suspending agent is isopropyl myristate.

* * * * *